(12) United States Patent
Rosenberg et al.

(10) Patent No.: US 6,387,401 B2
(45) Date of Patent: *May 14, 2002

(54) USE OF LIPIDS AS ADJUVENTS IN THE PRODUCTION OF SOLID MEDICINAL FORMS BY THE MELT EXTRUSION PROCESS

(75) Inventors: Joerg Rosenberg, Ellerstadt; Jörg Breitenbach, Mannheim, both of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/000,389

(22) PCT Filed: Aug. 21, 1996

(86) PCT No.: PCT/EP96/03667

§ 371 Date: Jan. 29, 1998

§ 102(e) Date: Jan. 29, 1998

(87) PCT Pub. No.: WO97/07786

PCT Pub. Date: Mar. 6, 1997

(30) Foreign Application Priority Data

Aug. 25, 1995 (DE) .......................................... 195 31 277

(51) Int. Cl.$^7$ ............................... A61K 9/20; B29B 9/00
(52) U.S. Cl. ........................ 424/464; 424/464; 424/465; 264/5; 264/13; 514/78
(58) Field of Search ................................ 424/400, 489, 424/464, 465; 264/13, 5

(56) References Cited

U.S. PATENT DOCUMENTS 5,641,516 A  6/1997  Grabowski et al. ......... 424/489

FOREIGN PATENT DOCUMENTS

| CA | 2188185 | 10/1995 |
|---|---|---|
| DE | 4413350 | 4/1994 |
| DE | 19504832 | 2/1995 |
| EP | 204 596 | 8/1989 |
| WO | 95/22319 | 8/1995 |
| WO | 96/14058 | 5/1996 |

OTHER PUBLICATIONS

Sucker et al., *Pharmazeutische Tech.*, 1991, pp. 259–260.

*Primary Examiner*—Gollamudi S. Kishore
(74) *Attorney, Agent, or Firm*—Keil & Weinkauf

(57) ABSTRACT

Lipids are used as aids in the production of solid drug forms by melt extrusion.

3 Claims, No Drawings

USE OF LIPIDS AS ADJUVENTS IN THE PRODUCTION OF SOLID MEDICINAL FORMS BY THE MELT EXTRUSION PROCESS

This application is a 371 of PCT/EP96/103/667 filed Aug. 21, 1996.

The present invention relates to the use of lipids as aids in the production of solid drug forms by melt extrusion.

The production of solid drug forms by melt extrusion is disclosed, for example, in U.S. Pat. No. 4,880,585, wherein the drug form is produced from the melt, which contains active ingredient and is still plastic, with the aid of a molding calender which directly molds tablets from the melt.

It has long been known that, in almost all cases when tablets are made from granules, satisfactory results are achieved only if a small amount of a lubricant is added to the formulations, after the granulation but before the tabletting, and this is deposited as a fine film on the outsides of the granule particles and thus prevents adhesion of the granules to the tabletting punches. The effect of these lubricants is very great although it is necessary to add only very small amounts to the granules (generally about 0.1 to 1% by weight; cf. H. Sucker, P. Fuchs. P. Speiser: Pharmazeutische Technologie; Georg Thieme Verlag, Stuttgart (1991), pages 259–260).

Known mold release agents for conventional processes are, for example, fatty acid esters or fatty acid salts, with only magnesium stearate normally being used in practice. Magnesium stearate is normally added to the granules which contain active ingredient and are ready before tabletting.

In the production of drug forms by melt extrusion in conjunction with a tabletting process such as calendering, it is crucial that the melt does not adhere to the surfaces of the calender rolls because, otherwise, there is no release from the molds. It also has to be taken into account in calendering to produce tablets that the compression process in the calender results in tablets which have a typical fin which is formed at the interface of the pairs of molding rolls which are in contact only at the surface. Following the calendering, this fin must be removed mechanically, generally after cooling/hardening of the melt tablets, in order to provide the tablets with a homogeneous surface structure. The success of this deflashing depends crucially on the consistency of the cooled melt containing active ingredient. This means that despite the calendering being satisfactory (no adhesion of the melt in the calender), deflashing of the resulting tablets is not necessarily possible. Many polymers form thermoplastic melts even in the presence of large amounts of active ingredients and/or ancillary substances, and these are highly flexible after cooling and can be flexed over wide ranges without breakage. In these cases, removal of the fins is very difficult and often completely impossible, although there are no problems with the extrusion and the calendering too.

Thus, it is crucial for the use of a formulation for producing tablets by melt extrusion/calendering that, besides the complete mixture having good thermoplasticity, in particular it is also possible to reduce the tendency to adhere during the calendering and control the plasticity of the cooled melt in order to ensure deflashing of the tablets.

Melt-processable cellulose derivatives such as hydroxypropylcellulose are, as water-soluble polymers, very suitable for producing tablets by solvent-free melt extrusion/calendering. It is possible by admixture of other ancillary substances, eg. HPMC (hydroxypropylmethylcellulose) polymers which are swellable in water, to control the dissolution times of such tablets in the gastrointestinal tract, as is disclosed, for example, in DE-A 4226753.

However, it has now been found that, in many cases when hydroxypropylcelluloses are used as water-soluble, thermoplastic polymer component, although the resulting melts can be extruded satisfactorily, they a) in many cases showed an extreme tendency to adhere during the calendering, b) did not permit removal of the fin because of excessive plasticity of the cooled melts (containing active ingredient) in the case of the calendered tablets, and c) caused considerable problems in cleaning the extruders because of the great tendency of the melt to adhere.

It is an object of the present invention to find aids which make it possible, especially when hydroxypropylcelluloses are used as matrix polymers in the production of drug forms by melt extrusion, to solve the abovementioned problems.

We have found that this object is achieved by using lipids as mold release agents and lubricants in the production of drug forms by melt extrusion.

The lipids which are suitable according to the invention are mono-, di- and triglycerides of naturally occurring fatty acids, for example glycerol monostearate, glycerol distearate, glycerol tristearate, glycerol tripalmitate, glycerol trimyristate, glycerol tribehenate, glycerol palmitate stearate or glyceride mixtures occurring in natural oils, preferably hydrogenated castor oil.

Ceramides are furthermore also suitable for this purpose.

Preferred lipids are, in particular, phospholipids, with phosphoglycerides such as lecithins being particularly preferred. Hydrogenated lecithins such as soybean and egg lecithins are very particularly preferred.

The lipids can be used in amounts of 0.1–10%, preferably 1–5%, of the total weight of the preparations containing active ingredient.

The preparations containing active ingredient can contain as matrix polymers melt-processable polymers, for example polyvinylpyrrolidone, copolymers of N-vinylpyrrolidone and vinyl acetate with up to 50% by weight of vinyl acetate, carboxyalkylcelluloses such as carboxymethylcelluloses, alkylcelluloses such as methylcellulose, hydroxyalkylcelluloses such as hydroxymethyl-, hydroxyethyl-, hydroxypropyl- and hydroxybutylcellulose, hydroxyalkylcelluloses such as hydroxyethylmethyl- and hydroxypropylmethylcellulose, or mixtures thereof.

Preferred polymers are hydroxypropylcelluloses and polymers based on vinylpyrrolidone.

Suitable active ingredients are all active ingredients which do not decompose under the conditions of melt extrusion.

The amount of the active component in the complete preparation can vary within wide limits depending on the activity and release rate. Thus, the content of active ingredient can be in the range from 0.1 to 90%, preferably from 0.5 to 60%, of the total weight of the preparation. The only condition is that the preparation is still melt-processable.

The preparations may furthermore contain conventional pharmaceutical ancillary substances such as bulking agents, colorants, disintegrants or stabilizers in conventional amounts.

Otherwise, the components are processed in a conventional way in extruders, preferably in single or twin screw extruders at a temperature in the range from 50 to 200° C. The shaping of the polymer melt which contains active ingredient and is free of solvent to give the preparations according to the invention can take place, for example, by calendering the extrudate and by converting the extrudate with rotating knives into pellets which have identical volumes and have a solidified surface but are still moldable, and subsequently compressing to tablets in conventional tabletting machines.

It is possible to mix the ancillary substances into the melt or solution of active ingredients and polymers. It is furthermore possible to incorporate the ancillary substances together with the active ingredient into the polymer melt. In addition, mixtures of ancillary substances, the active ingredient and the polymers can be directly melted. It is generally customary for a physical mixture of ancillary substances, active ingredients and the polymers to be melted together.

It has been found, surprisingly, that addition of even small amounts of lipids is able to prevent adhesion of the melts containing active ingredient.

Addition of only 3% by-weight of lecithin reduces the melt adhesion of the extruded composition so much that the formulations can be calendered without restrictions. The cleaning of the extruder to remove the otherwise viscous, highly adhesive melt residues is considerably simplified because lecithin-containing formulas show scarcely any adhesion to metal and can be removed en bloc from the metal parts of the extruder which are still hot after completion of the extrusion. The plasticity of the cooled 40 melt is also beneficially affected so that deflashing of the tablets (removal of fins) takes place considerably better.

Examples 1 to 20

All the tests were carried out in a twin screw extruder (ZSK-40 extruder from Werner und Pfleiderer, Stuttgart). The extruder comprised 4 heatable sections, and it was possible to heat the extruder head and the slit die separately. The temperature settings are to be found in the table. The extruded melt was discharged in the form of a strip 12–14 cm wide through a slit die and subsequently directly compressed to tablets in a molding calender consisting of a pair of counter-rotating molding rolls (coolable). The tablets had an elongate, rod-like shape (oblong tablets without bar). The raw materials listed in the table have previously been mixed in a gyro-wheel mixer and fed as mixture into the extruder via a weigh feeder delivering 20 to 30 kg/h. The extruder conveyor was operated in all cases at 100 to 150 rpm.

For comparison purposes, formulations in which no lipid was used were processed. Although extrusion was possible in all these cases, calendering was not, because it was impossible to remove the tablets from the pairs of molding rolls in the calender. In addition, cleaning of the parts of the extruder coming into contact with the product was considerably more difficult in these cases (composition strongly adherent to metal surfaces) than with lipid-containing formulations.

TABLE 1

| Ex. No. | Active ingredient (a) | Polymer (b) | Ancillary substance (c) | Lipid (d) + (e) | Weight a:b:c:d:e | T 1 | T 2 | T 3 | T 4 | T H | T D |
|---|---|---|---|---|---|---|---|---|---|---|---|
| 1 | Verapamil HCl | HPC | HPMC-100 | Cast. | 46/29/20/5/0 | 80 | 100 | 100 | 100 | 100 | 100 |
| 2 | Verapamil HCl | HPC | HPMC-100 | Lec. | 49/38/10/3/0 | 80 | 100 | 110 | 110 | 110 | 110 |
| 3 | Verapamil HCl | HPC | HPMC-4 | Lec. | 48/32/18/3/0 | 80 | 100 | 110 | 110 | 110 | 110 |
| 4 | Verapamil HCl | HPC | HPMC-4 | Lec. | 50/37/10/3/0 | 80 | 100 | 110 | 110 | 110 | 110 |
| 5 | Verapamil HCl | HPC | HPMC-100 | Lec. + cast. | 50/35/10/2.5/2.5 | 80 | 100 | 110 | 110 | 110 | 110 |
| 6 | Verapamil HCl | HPC | HPMC-100 | Cast. | 50/33/10/7/0 | 80 | 100 | 105 | 110 | 110 | 110 |
| 7 | Nifedipine | HPC | HPMC-100 | Lec. | 7.7/69.3/20/3/0 | 90 | 110 | 100 | 110 | 110 | 115 |
| 8 | Nifedipine | HPC | HPMC-100 | Lec. | 23.1/51.9/20/5/0 | 90 | 110 | 110 | 110 | 120 | 120 |
| 9 | Nifedipine | HPC | HPMC-100 | Cast. | 23.1/51.9/20/5/0 | 90 | 110 | 120 | 120 | 120 | 120 |
| 10 | 1) | HPC | — | — | 20/80/0/0/0 | 140 | 140 | 140 | 140 | 140 | 130 |
| 11 | 1) | HPC | — | — | 21.9/78.1/0/0/0 | 140 | 140 | 140 | 140 | 140 | 130 |
| 12 | Placebo | HPC | Mannitol | — | 0/60/40/0/0 | 90 | 120 | 100 | 100 | 120 | 120 |
| 13 | Placebo | HPC | — | — | 0/100/0/0/0 | 100 | 120 | 110 | 120 | 120 | 120 |
| 14 | 1) | HPC | Mannitol | Lec. | 18.2/36.8/40/5/0 | 90 | 120 | 100 | 100 | 110 | 110 |
| 15 | Placebo | HPC | Mannitol | Lec. | 0/55/40/5/0 | 90 | 120 | 100 | 100 | 120 | 120 |
| 16 | 1) | HPC | Mannitol | Lec. | 9/46/40/5/0 | 90 | 120 | 100 | 100 | 110 | 110 |
| 17 | 2) | HPC | HPMC-100 | — | 10.4/49.6/40/0/0 | 130 | 110 | 110 | 110 | 110 | 115 |
| 18 | Placebo | HPC | HPMC-100 | Lec. | 0/58/40/2/0 | 90 | 110 | 100 | 110 | 110 | 110 |
| 19 | 2) | HPC | HPMC-100 | Lec. | 19.8/38.2/40/2/0 | 90 | 105 | 95 | 105 | 105 | 110 |
| 20 | Placebo | VA-64 | Lactose | Lec. | 0/55/40/5/0 | 80 | 100 | 110 | 110 | 120 | 130 |

1)3,4-Dimethyl-7-(2-isopropyl-1,3,4-thiadiazol-5-yl)-methoxy-cumarin
2)5-(N-Methylamino)-2-(1-isopropyl)-2-(3,4,5-trimethoxyphenyl)undecanonitrile hydrochloride
HPC Hydroxypropylcellulose (Klucel, Hercules)
VA-64 Copolyvidone DAB (Kollidon VA-64, BASF)
HPMC-100 Hydroxypropylmethylcellulose (Methocel K 100 M, Colorcon)
HPMC-4 Hydroxypropylmethylcellulose (Methocel K 4 M, Colorcon)
Lec. Hydrogenated soybean lecithin (from Stern)
Cast. Hydrogenated castor oil (Cutina HR, Henkel)
T 1 to T 4 Temperatures of extruder sections 1–4 (° C.)
T H Temperature of extruder head (° C.)
T D Temperature of extruder die (° C.)

We claim:

1. A process for producing a solid pharmaceutical composition in tablet form by melt extrusion, which process consists essentially of mixing an active ingredient, a water-soluble thermoplastic matrix polymer and a lipid;

heating the mixture until a solvent-free, polymer melt is formed;

extruding the melt into a tabletting molding calender;

allowing the melt to cool; and removing the formed solid pharmaceutical composition in the form of a tablet from the molding calender;

wherein the lipid is used in amounts of 1–5% of the total weight of the composition and functions as a mold release agent and lubricant.

2. The process of claim 1, wherein the lipid is a phospho glycerine.

3. The process of claim 1, wherein the lipid is a lecithin.

* * * * *

UNITED STATES PATENT AND TRADEMARK OFFICE
CERTIFICATE OF CORRECTION

PATENT NO.    : 6,387,401 B2                                                    Page 1 of 1
DATED         : May 14, 2002
INVENTOR(S)   : Rosenberg et al.

It is certified that error appears in the above-identified patent and that said Letters Patent is hereby corrected as shown below:

<u>Column 6,</u>
Line 6, "phospho" should be -- phosphor --.

Signed and Sealed this

Sixteenth Day of July, 2002

Attest:

JAMES E. ROGAN
Attesting Officer    Director of the United States Patent and Trademark Office